United States Patent
Boeck et al.

(10) Patent No.: US 10,787,414 B2
(45) Date of Patent: Sep. 29, 2020

(54) DIISOPENTYL TEREPHTHALATE

(71) Applicant: Evonik Degussa GmbH, Essen (DE)

(72) Inventors: Florian Boeck, Münster (DE); Michael Grass, Haltern am See (DE); Benjamin Woldt, Bochum (DE); André Huber, Marl (DE); Christine Blex, Marl (DE); Ulrike Blumenthal, Marl (DE)

(73) Assignee: Evonik Operations GmbH, Essen (DE)

( * ) Notice: Subject to any disclaimer, the term of this patent is extended or adjusted under 35 U.S.C. 154(b) by 250 days.

(21) Appl. No.: 15/867,020

(22) Filed: Jan. 10, 2018

(65) Prior Publication Data

US 2018/0208541 A1    Jul. 26, 2018

(30) Foreign Application Priority Data

Jan. 20, 2017 (EP) .................................. 17152394

(51) Int. Cl.
*C08K 5/12* (2006.01)
*C07C 67/02* (2006.01)
*C07C 67/08* (2006.01)
*C07C 69/82* (2006.01)

(52) U.S. Cl.
CPC .............. *C07C 69/82* (2013.01); *C07C 67/02* (2013.01); *C07C 67/08* (2013.01); *C08K 5/12* (2013.01); *C07C 2601/16* (2017.05)

(58) Field of Classification Search
CPC ......... C07C 69/82; C07C 67/02; C07C 67/08; C07C 2601/16; C08K 5/12

USPC ......................................................... 524/296
See application file for complete search history.

(56) References Cited

U.S. PATENT DOCUMENTS

| | | | |
|---|---|---|---|
| 7,964,658 B2 | 6/2011 | Grass | |
| 8,329,796 B2 | 12/2012 | Grass | |
| 2013/0310472 A1 | 11/2013 | Becker et al. | |
| 2013/0310473 A1 | 11/2013 | Becker et al. | |
| 2013/0317152 A1 | 11/2013 | Becker et al. | |
| 2013/0317153 A1 | 11/2013 | Grass et al. | |
| 2016/0237243 A1* | 8/2016 | Woldt | C07C 67/03 |
| 2016/0237244 A1* | 8/2016 | Boeck | C07C 67/03 |
| 2017/0088691 A1 | 3/2017 | Woldt et al. | |

FOREIGN PATENT DOCUMENTS

| | | |
|---|---|---|
| EP | 1808457 B1 | 7/2008 |
| EP | 3059221 A1 | 8/2016 |
| EP | 3059222 A1 | 8/2016 |
| EP | 3059223 A1 | 8/2016 |
| WO | 2010071717 A1 | 6/2010 |

* cited by examiner

*Primary Examiner* — Kelechi C Egwim
(74) *Attorney, Agent, or Firm* — Nexsen Pruet PLLC; Philip P. McCann

(57) ABSTRACT

A mixture of isomeric dipentyl terephthalates, pentyl radicals of which are n-pentyl radicals to an extent of less than 60 mol %, characterized by a low viscosity which does not increase significantly even at temperatures below 40° C. Plastisols comprising these mixtures have a low plastisol viscosity which moreover increases only to a minor degree with time.

19 Claims, 11 Drawing Sheets

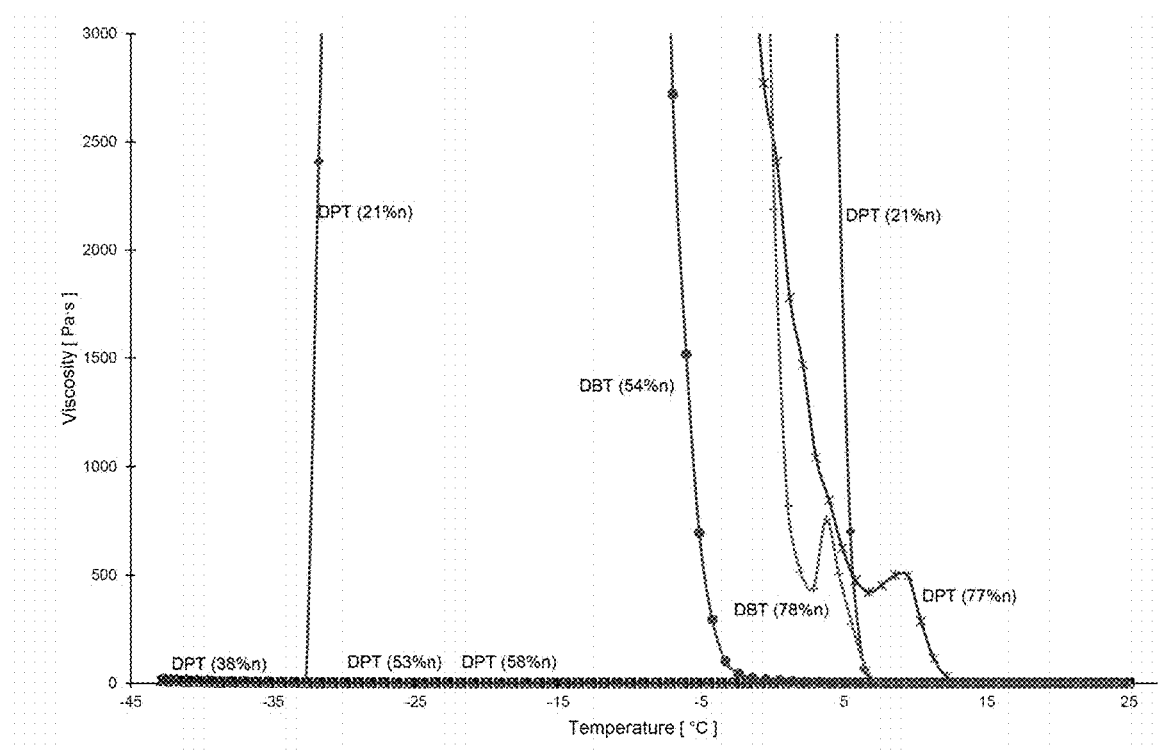
Figure 1: Low temperature viscosity of the ester mixtures from Examples 1 to 8

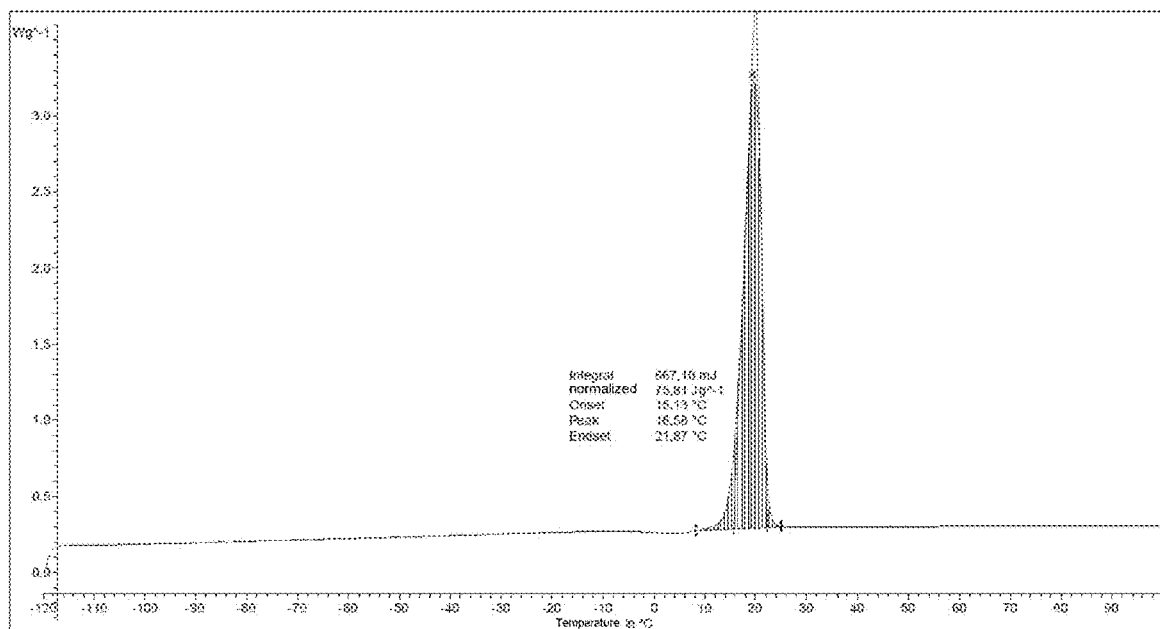
Figure 2: DSC of DPT (0‰n, ↑endo)

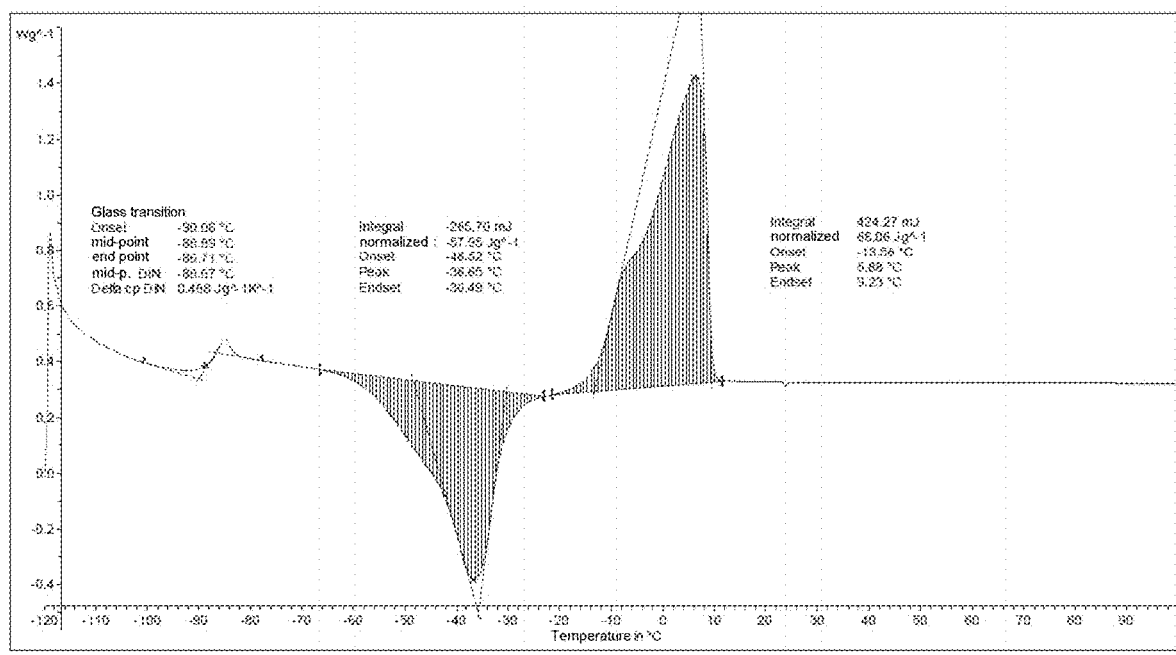
Figure 3: DSC of DPT (21%n, ↑endo)

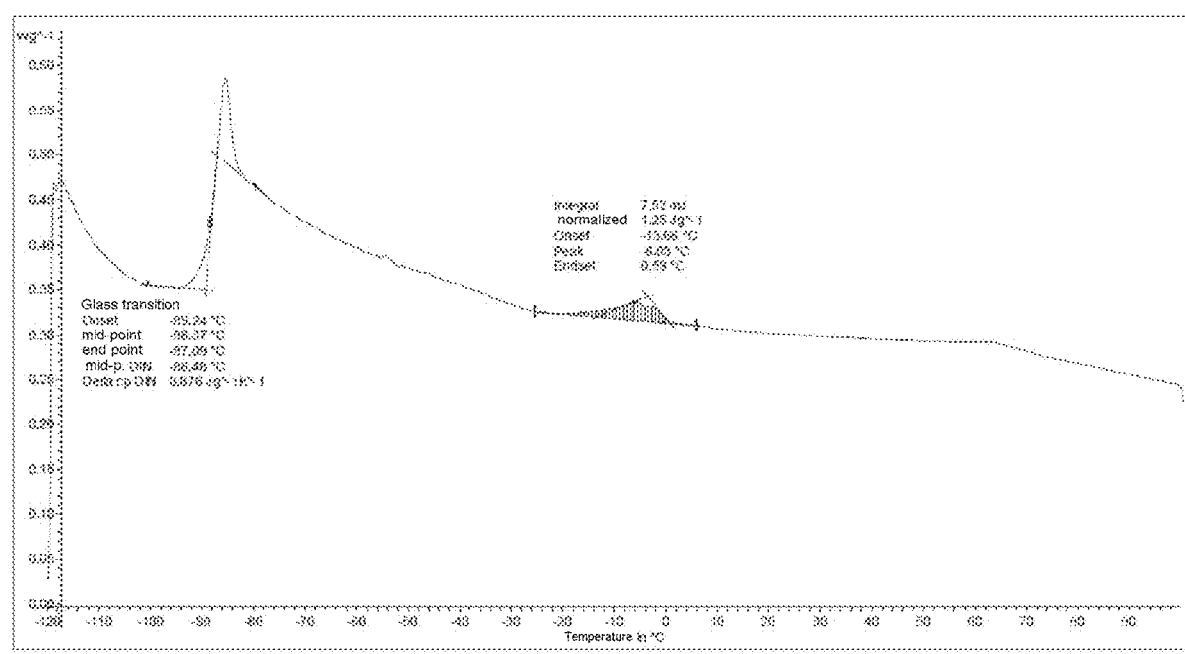
Figure 4: DSC of DPT (38%n, ↑endo)

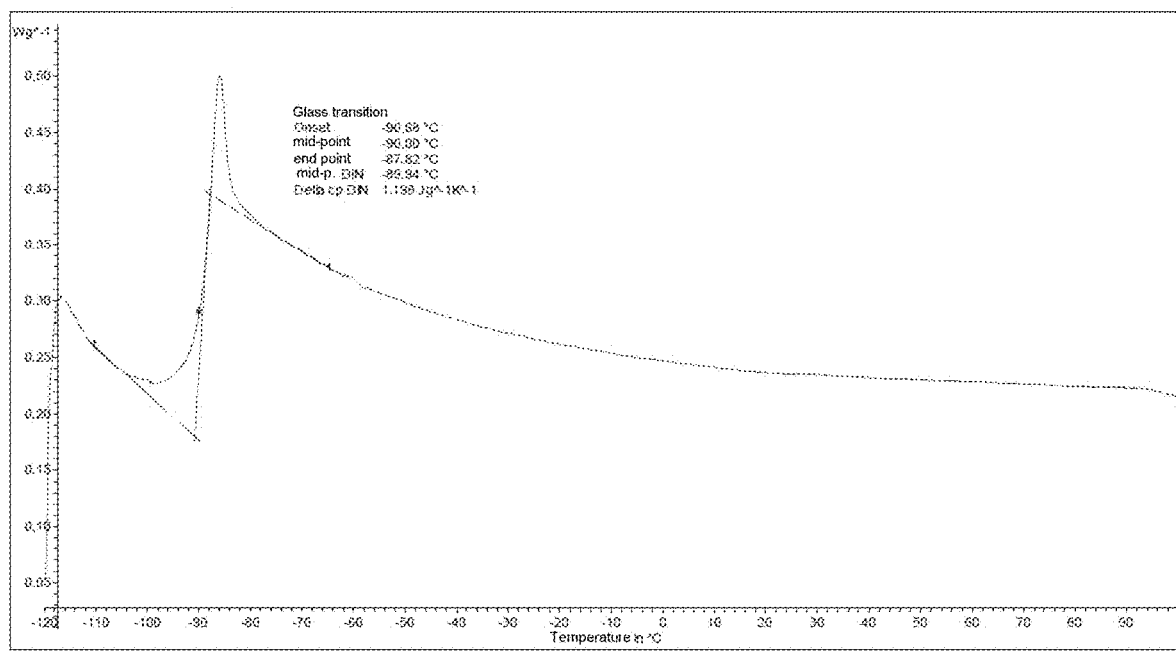
Figure 5: DSC of DPT (53%n, ↑endo)

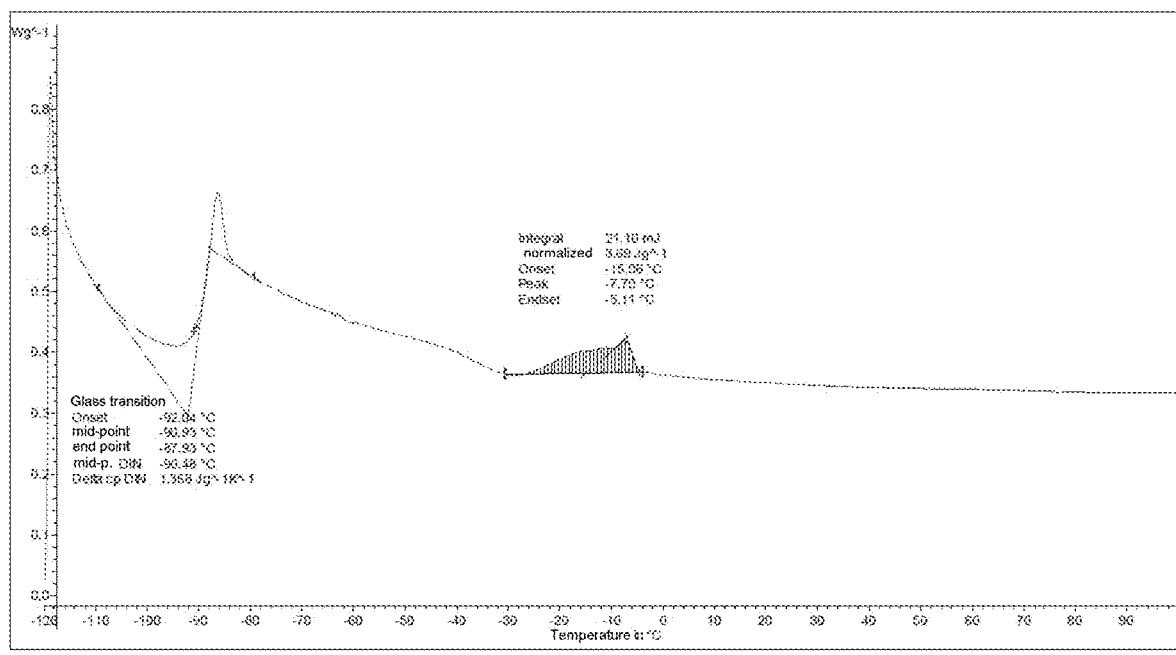
Figure 6: DSC of DPT (58%n, ↑endo)

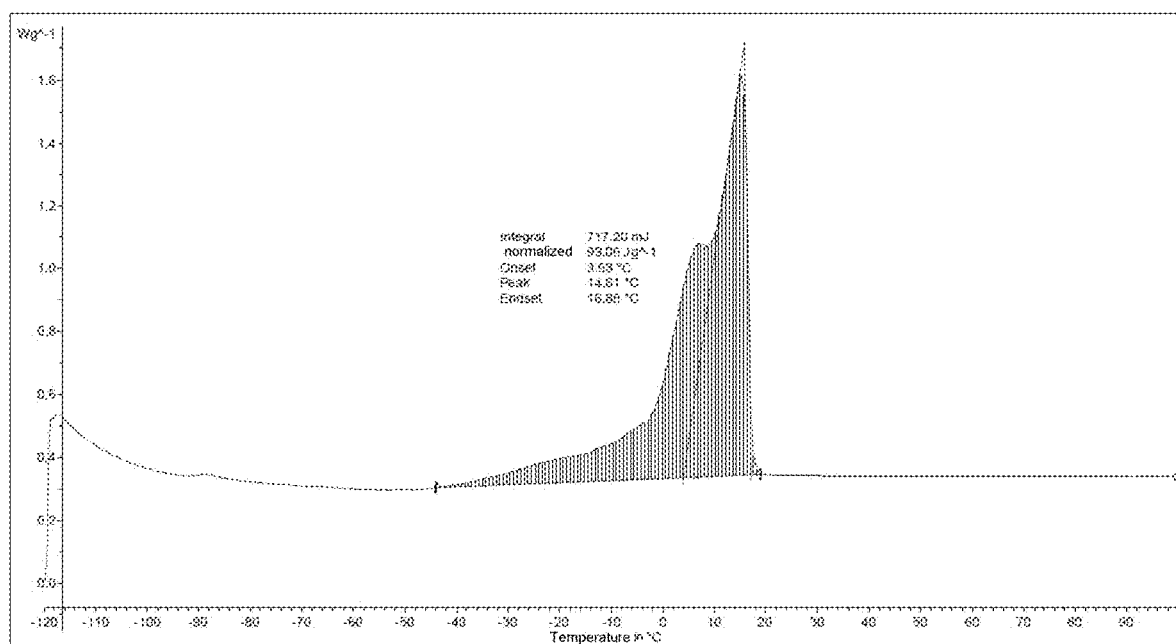
Figure 7: DSC of DPT (77%n, ↑endo)

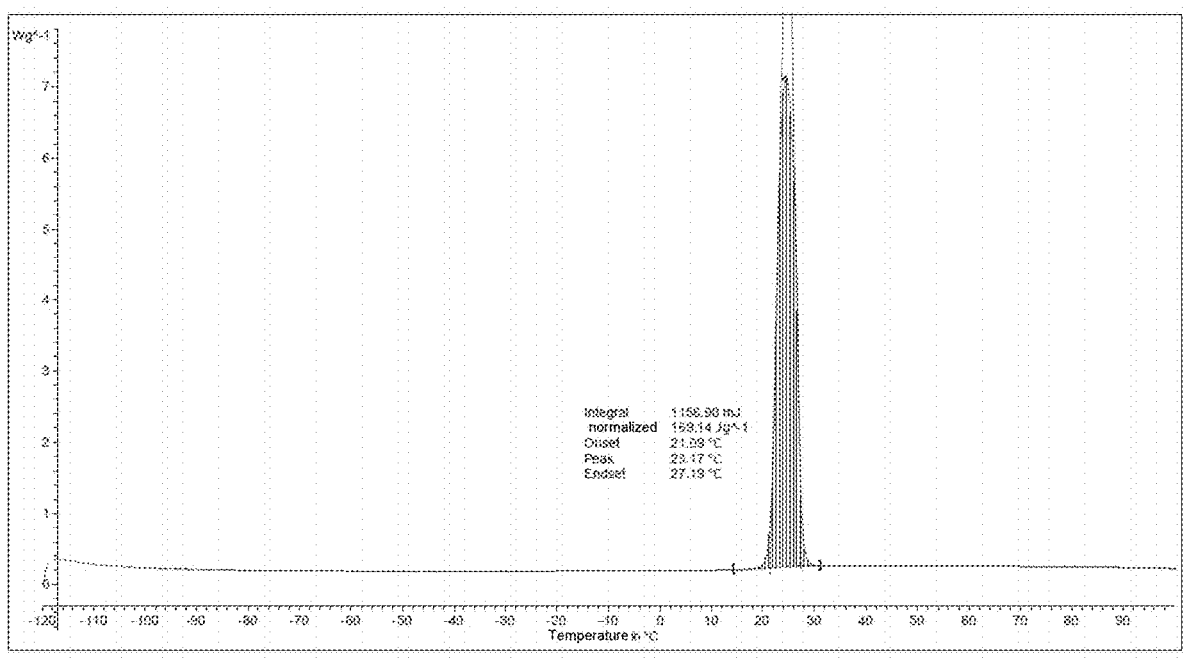
Figure 8: DSC of DPT (100%n, ↑endo)

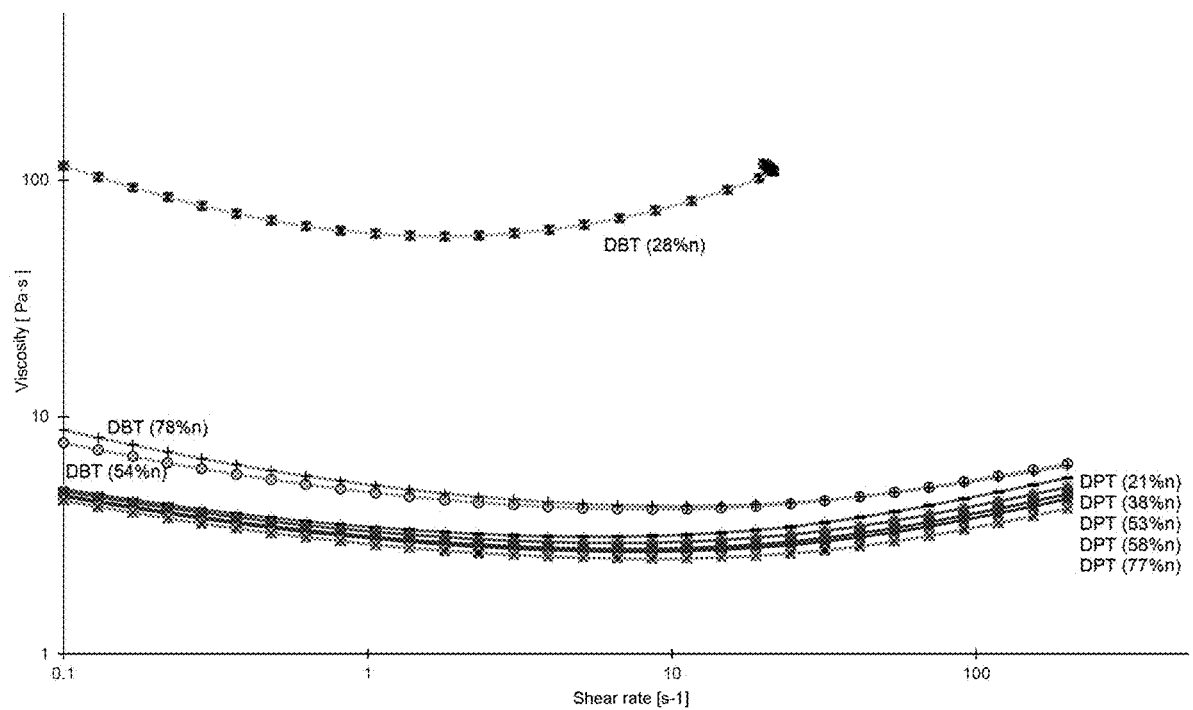
Figure 9: Plastisol viscosity after 7 days' storage at 25°C

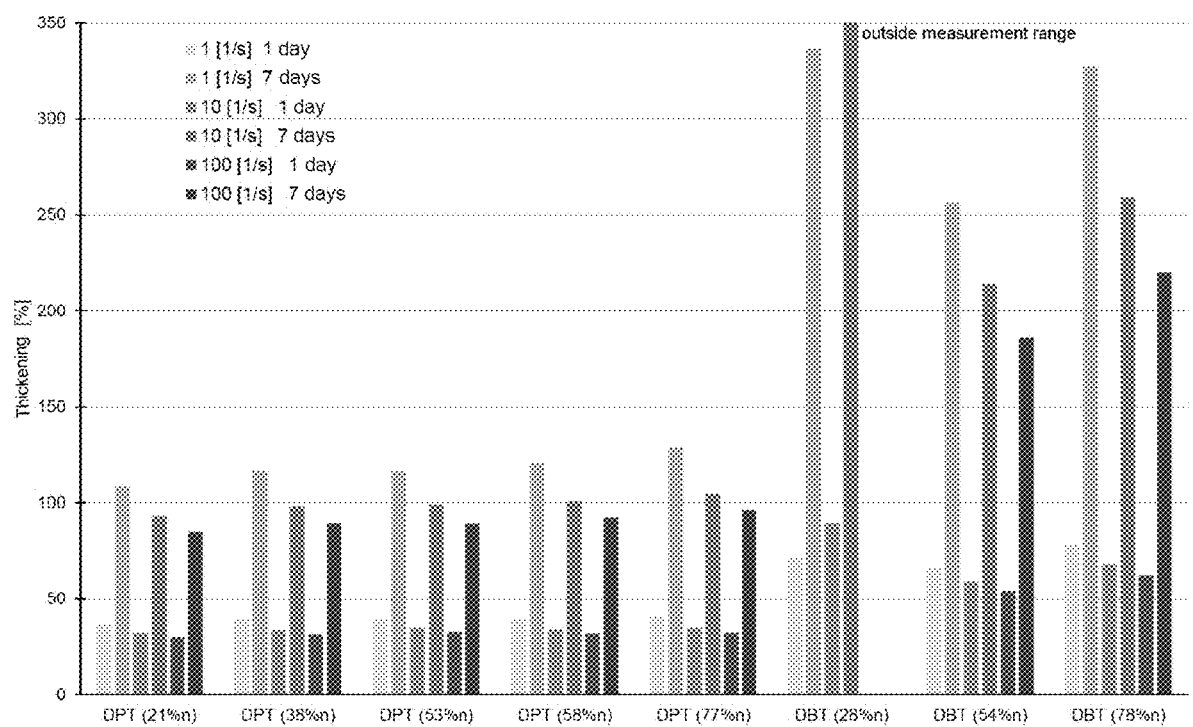
Figure 10: Thickening of the plastisols

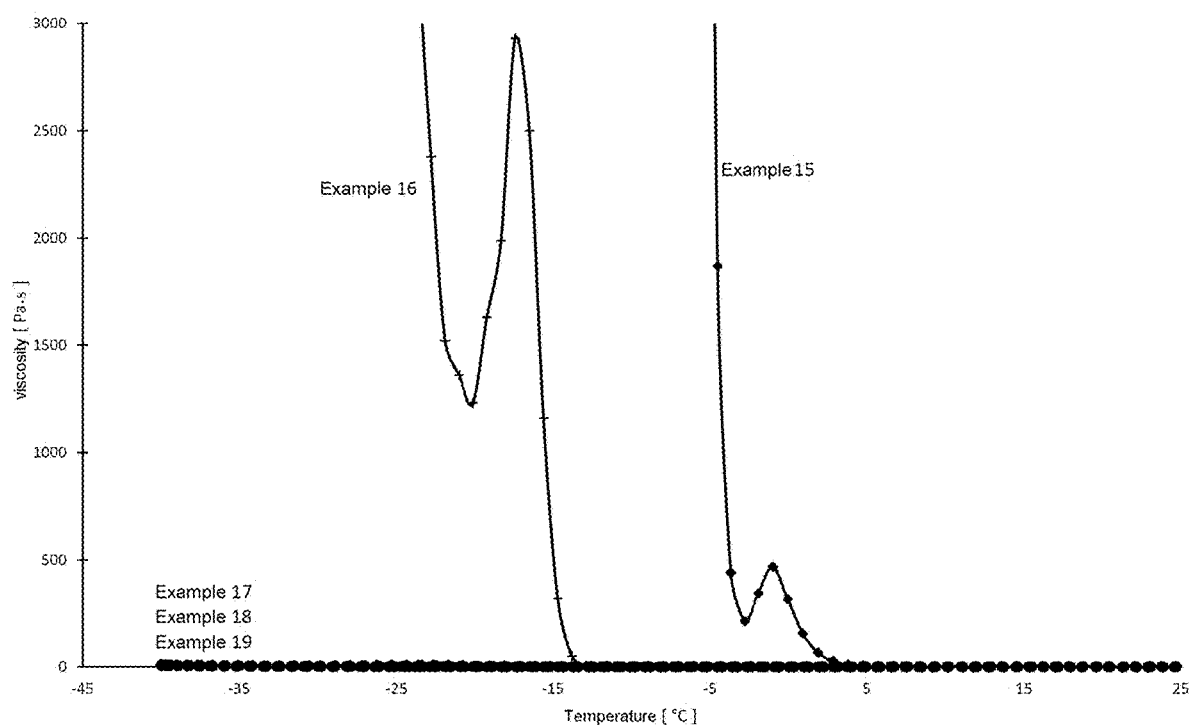
Figure 11: Low temperature viscosity of the ester mixtures from Examples 15 to 19

DIISOPENTYL TEREPHTHALATE

This application claims the benefit of European Application No. 17152394.7 filed on Jan. 20, 2017, the disclosure of which is expressly incorporated herein by reference.

FIELD

The present invention relates to diisopentyl terephthalate, preparation thereof, plasticizer mixtures, plastisols and commercial products comprising diisopentyl terephthalate and also to the use of diisopentyl terephthalate as plasticizer and also for lowering viscosity.

BACKGROUND

Within the area of the plasticizers for polymers, terephthalic esters have already been used for a number of years as a replacement for or supplement to phthalic esters. The most important terephthalic ester commercially is diethylhexyl terephthalate, which is often also referred to, in simplified form, as dioctyl terephthalate. Terephthalic esters which comprise alcohol radicals having fewer or more than 8 carbon atoms are likewise described in the prior art. In the context of this text, alcohol radicals are also referred to as alkyl radicals (of the esters).

Dependent on factors including the number of carbons in the alcohol radicals of the ester functions, the terephthalic esters have different properties and are suitable accordingly to a greater or lesser extent for different plasticizer applications. For instance, relatively short-chain terephthalic esters tend to gel at lower temperatures than their longer-chain homologues. A low gelling temperature in a plasticizer represents a positive property particularly in the context of plastisol processing, since this processing can be carried out at lower temperatures and, moreover, higher processing throughputs can be achieved than in the case of the processing of plastisols which comprise plasticizers having a high gelling temperature.

At the same time, however, terephthalic esters with a low molecular weight and, accordingly, a low number of carbons in the alcohol radical have a higher volatility than their heavier homologues. High volatility in a plasticizer is a serious disadvantage, since leakage of the plasticizer not only alters the properties of the plasticized polymer and hence reduces the longevity of the product but also releases plasticizer into the environment.

The release of plasticizer is a problem, moreover, since in the fields of interior applications, medicinal products, toys, cables and in the automobile sector for example, marketing of the products requires compliance with standards which govern the maximum amount of organic compounds emerging from a product, in order to ensure the necessary safety for consumers and the environment. Thus, for example, in Germany, the construction products Health Evaluation Committee (AgBB), in harmony with the Construction Products Regulation (No. 305/2011) agreed by the European Parliament, regulates the avoidance and limitation of pollutants in interior spaces. From a health standpoint, accordingly, construction products, and hence also plasticizer-containing products, are deemed suitable for use in interior spaces in buildings only when certain limit values for emitted VOCs (Volatile Organic Compounds) and SVOCs (Semi-volatile Organic Compounds) are not exceeded in a standardized measurement process. In accordance with DIN ISO 16000-6, organic compounds classed as SVOCs are those which are in the retention range of greater than n-C16-paraffin up to n-C22-paraffin on a non-polar column (AgBB—Evaluation Scheme for VOC from construction products, 2015 status). Products which have higher-than-permitted emissions can be used only when additional measures, such as the application of an emission barrier layer of varnish for example, prevent the maximum-permitted emissions quantity being exceeded. The necessity for such additional measures, however, restricts the freedom in the formulation of the plasticizers in products and therefore makes it more expensive to use plasticizers having a VOC or SVOC classification. Moreover, as a result of the necessity for such additional protective layers, further difficulties may arise, such as, for example, increased susceptibility of a varnish-protected, SVOC-containing product to scratches or flaking.

Patent EP 1 808 457 B1 discloses that terephthalic esters having 4 to 5 carbon atoms in the longest carbon chain of the alcohol radical are particularly well-suited as rapidly gelling plasticizers. Dibutyl terephthalates should be classified as SVOCs however and their use therefore is linked to the disadvantages described above. Moreover, some application-relevant properties of dibutyl terephthalates depend to a significant degree on the isomer distribution of the butyl radicals and the viscosity of dibutyl terephthalate-containing pastes increases markedly on storage. Both properties have a disadvantageous effect in terms of use.

Application WO 2010/071717 A1 describes terephthalic acid diesters of $C_5$-$C_7$-alcohols and focuses distinctly on diheptyl terephthalate. Diheptyl terephthalate gels at significantly higher temperatures compared to dipentyl terephthalate however and is therefore less well suited as a fast fuser than dipentyl terephthalate.

Application-relevant properties of the plasticizers are not only a function of the carbon number in the alcohol radicals of the ester functions but also of the degree of branching of these alcohol radicals. For instance, the text book Plasticisers, Principles and Practice, Alan S. Wilson, The Institute of Materials 1995, explains with regard to the phthalates that plasticizers have particularly advantageous properties, in particular a low viscosity and a low plastisol viscosity, when the alcohol radicals of the ester functions have on average a low degree of branching. In agreement with this, document EP 1 808 457 B1 highlights terephthalic esters as advantageous when the alkyl radicals thereof are predominantly linear pentyl radicals. A person skilled in the art transfers these findings about advantageous isomer distributions of phthalates and terephthalates to other plasticizers which also comprise ester functions.

As a consequence of this, the demand for linear alcohols for plasticizer production is high. However, since their proportion in hydroformylation products is only controllable within limits, the price of hydroformylation products containing a high proportion of linear alcohols is generally high, while at the same time sales potential is sought for branched hydroformylation products, that is to say for branched plasticizer alcohols.

The low viscosity of plasticizers already referred to above as advantageous and the low plastisol viscosity of the plastisols produced from the plasticizers are of high significance in terms of performance since liquids can only be reliably pumped up to a viscosity of circa 1000 Pa·s using conventional pumps. If a plasticizer or a plastisol has a viscosity above this threshold, transport is only possible with the aid of expensive special pumps or at elevated temperature which reduces the viscosity of the medium to be pumped.

SUMMARY

It was an object of the present invention, accordingly, to overcome some, and preferably all, of the disadvantages of the prior art stated above.

The intention preferably was to provide a plasticizer which in order to ensure maximum freedom in formulation, does not fall within the definitions of the compounds regulated by German or international directives. With preference, a plasticizer based on terephthalic esters should be provided in this case.

The plasticizer should be of economic interest, i.e. should enable a high raw material utilization and at the same time should preferably be processable with the lowest possible expenditure in terms of apparatus.

The object is achieved by a diisopentyl terephthalate according to claim 1.

BRIEF DESCRIPTION OF THE DRAWINGS

FIG. 1 representatively shows low temperature viscosity of the ester mixtures from Example 1 to 8;
FIG. 2 representatively shows DSC of DPT(0% n);
FIG. 3 representatively shows DSC of DPT(21% n);
FIG. 4 representatively shows DSC of DPT(38% n);
FIG. 5 representatively shows DSC of DPT(53% n);
FIG. 6 representatively shows DSC of DPT(58% n);
FIG. 7 representatively shows DSC of DPT(77% n);
FIG. 8 representatively shows DSC of DPT(100% n);
FIG. 9 representatively shows plasticol viscosity after 7 days storage at 25° C.;
FIG. 10 representatively shows thickening fo the plastisols; and
FIG. 11 representatively shows low temperature viscosity of the ester mixtures from examples 15 to 19.

DETAILED DESCRIPTION

The present invention provides diisopentyl terephthalate (DPT), the pentyl radicals of which are n-pentyl radicals to an extent of less than 60 mol %.

In other words, the advantages are achieved by a mixture of dipentyl terephthalates having isomeric branched and unbranched pentyl radicals, in which less than 60 mol % of the pentyl radicals are linear pentyl radicals (n-pentyl radicals). This mixture is referred to hereinafter as diisopentyl terephthalate according to the invention, (pentyl) ester mixture according to the invention or also as DPT for short.

In the context of this text, reference is often made simply to alkyl radicals when the radicals of the ester originating from the alcohol are discussed. For instance, the radical of an ester function originating from a pentanol is simply referred to as a pentyl radical.

It has been found, surprisingly, that plastisols comprising DPT according to the invention have a low plastisol viscosity which moreover increases only to a minor degree with time. Plastisols comprising DPT according to the invention are accordingly particularly storage-stable. It has been found that both properties—the low plastisol viscosity and the good storage stability—are firstly exceptionally advantageous within the claimed range of the isomer composition of the DPT and secondly vary surprisingly little within this range and so are virtually independent of the isomer distribution. The same applies to the gelling temperature of the plastisols. Therefore, DPT according to the invention always has advantageous, reliably predictable properties for those skilled in the art tasked with their use even in the case of variation of the isomer distribution and even if at the time unaware of the same.

It has also been found that the DPT according to the invention itself also has a low viscosity and increases its viscosity only at surprisingly low temperatures. This enables the processing of DPT according to the invention with low expenditure in terms of apparatus since the DPT can be conveyed by means of normal pumps even at low or fluctuating temperatures and without heated pipelines and tanks or special pumps being required to ensure that the DPT can be pumped.

Against the background of the supposed superiority of linear alkyl radicals in plasticizers taught in the literature, DPT having a high proportion of branched pentyl radicals in accordance with the invention can also surprisingly be used advantageously. This enables the economically and ecologically advantageous use of hydroformylation products comprising a high proportion of branched pentanols.

The mixture according to the invention of dipentyl terephthalates having isomeric branched and unbranched pentyl radicals, in which less than 60 mol % of the pentyl radicals are linear pentyl radicals (n-pentyl radicals), can neither be classified as VOC nor as SVOC according to the customary test described above since none of the mixture components present in the retention range is less than or equal to n-C22-paraffin. Consequently, its use—in contrast to the use of mixtures of isomeric dibutyl terephthalates—is not regulated by German or international guidelines.

By way of preference, at least 2 mol %, preferably at least 10 mol % of the pentyl radicals in the DPT according to the invention are n-pentyl radicals. In a preferred diisopentyl terephthalate, more than 20 mol % of the pentyl radicals, with preference more than 22.5 mol %, more preferably more than 25 mol %, more preferably more than 27.5 mol % and especially more than 30 mol % or more than 35 mol % of the pentyl radicals in the ester mixture are n-pentyl radicals.

In addition to the linear n-pentyl radicals, the DPT according to the invention comprises branched pentyl radicals. A branched pentyl radical is preferably a methylbutyl radical. Accordingly, preference is given to DPT in which the branched pentyl radicals in the ester mixture consist of methylbutyl radicals to an extent of at least 50 mol %, preferably to an extent of at least 60 mol %, further preferably to an extent of at least 70 mol %, still further preferably to an extent of at least 80 mol %, even more preferably to an extent of at least 90 mol % and especially to an extent of at least 95 mol %.

It is advantageous if the branched isomeric pentyl radicals in the ester mixture have a large proportion of 2-methylbutyl radicals. In a preferred embodiment, therefore, at least 50 mol %, preferably at least 60 mol %, more preferably at least 70 mol %, further preferably at least 80 mol %, especially preferably at least 90 mol % and especially at least 95 mol % of the branched isomeric pentyl radicals incorporated in the ester mixture are 2-methylbutyl radicals. The DPT according to the invention preferably comprises 20 to 95 mol %, preferably 30 to 85 mol % and especially 40 to 75 mol % of 2-methylbutyl radicals, based on all pentyl radicals present.

A preferred subject matter of the present invention is a diisopentyl terephthalate (DPT), pentyl radicals of which are n-pentyl radicals to an extent of more than 2 mol % and less than 60 mol %; the remaining pentyl radicals in this DPT are branched, wherein at least 50 mol %, preferably at least 60 mol % and especially at least 70 mol % thereof are 2-methylbutyl radicals. A DPT of this kind according to the invention is characterized by a low viscosity, which does not increase significantly even on lowering the ambient temperature to −30° C. and below. A DPT of this kind can be reliably processed with minimal effort even at very low and fluctuating temperatures. The advantageousness of such a DPT is demonstrated in Examples 15 to 19.

In a particularly preferred embodiment, the DPT according to the invention consists to an extent of at least 75 mol %, more preferably to an extent of at least 90 mol % and especially to an extent of at least 95 mol % of esters containing—preferably exclusively—2-methylbutyl and/or linear pentyl radicals, where the molar ratio of 2-methylbutyl radicals to linear pentyl radicals in this ester mixture is preferably in the range from 95:5 to 40:60, especially in the range from 70:30 to 40:60.

A particularly low viscosity in the plastisol is achieved when the branched isomeric pentyl radicals in the ester mixture consist of a significant to large proportion of 3-methylbutyl radicals. In such a case, at least 10 mol %, preferably at least 20 mol %, more preferably at least 30 mol %, further preferably at least 40 mol %, with preference at least 50 mol %, preferably at least 60 mol %, further preferably at least 70 mol %, especially preferably at least 80 mol % and especially at least 90 mol % of the branched isomeric pentyl radicals incorporated in the ester mixture are 3-methylbutyl radicals. It may additionally be advantageous when the DPT according to the invention consists to an extent of at least 75 mol % and especially to an extent of at least 90 mol % of esters containing—preferably exclusively—3-methylbutyl and/or linear pentyl radicals, and at the same time the molar ratio of 3-methylbutyl radicals to linear pentyl radicals is in the range from 95:5 to 40:60, especially in the range from 70:30 to 40:60.

As already described, DPT according to the invention has a low viscosity down to low temperatures and can therefore be pumped over a wide temperature range without difficulty and without further inconvenience. DPT preferably has a viscosity at temperatures above 10° C. of less than 1000 Pa·s, preferably less than 500 Pa·s. The viscosity is advantageously at values of less than 1000 Pa·s at temperatures above 5° C., preferably at temperatures above 0° C. and especially at temperatures above −5° C. . The viscosity is preferably determined using a Rheometer by means of an oscillating plate-plate system, preferably with a measurement gap width of 0.5 mm. With particular preference, the viscosity is measured as described in the experimental section, Example 9.

It has been found, surprisingly, that although mixtures of isomeric dipentyl terephthalates according to the invention (inventive DPT) for the most part have melting points in the range below −10° C. (onset) according to DSC measurement (Differential Scanning Calorimetry), at these and even lower temperatures they have a sufficiently low viscosity in order to still be able to be conveyed using normal pumps. It has been found that DPT according to the invention having a Boeck factor of less than 100, preferably less than 90, more preferably less than 70, particularly preferably less than 50 and especially less than 30 or even less than 10, can be pumped even at low temperatures with low expenditure in terms of apparatus and energy. The determination of the Boeck factor is illustrated in the experimental section. The Boeck factor of the DPT according to the invention preferably has values of less than 100, preferably less than 90, preferably less than 50, especially less than 10.

The effect of the low viscosity even at low temperatures preferably occurs also in a mixture of the DPT according to the invention with one or more plasticizers, particularly in a mixture with at least one primary plasticizer. The present invention therefore also relates to a mixture comprising DPT according to the invention and at the least one additional plasticizer.

Suitable additional plasticizers are adipates, benzoates, examples being monobenzoates or glycol dibenzoates, chlorinated hydrocarbons, citrates, cyclohexanedicarboxylates, epoxidized fatty acid esters, epoxidized vegetable oils, epoxidized acylated glycerides, furandicarboxylates, phosphates, phthalates (preferably in very small amounts), succinates, sulfonamides, sulfonates, terephthalates, trimellitates or oligomeric or polymeric esters based on adipic, succinic or sebacic acid. Particularly preferred are alkyl benzoates, dialkyl adipates, glycerol esters, trialkyl citrates, acylated trialkyl citrates, trialkyl trimellitates, glycol dibenzoates, other dialkyl terephthalates, esters of furandicarboxylic acid, dialkanoyl esters of dianhydrohexitols (e.g. isosorbitol) and dialkyl esters of 1,2-, 1,3- or 1,4-cyclohexanedicarboxylic acid. In a particularly preferred embodiment, the mixture of the plasticizers comprises less than 5% by mass and especially less than 0.5% by mass phthalate-containing compounds. In a further preferred embodiment, the additional plasticizer is not a diheptyl terephthalate.

The ratio of DPT according to the invention to additional plasticizer is preferably from 80:20 to 3:97, preferably from 60:40 to 10:90, particularly preferably from 50:50 to 20:80 and especially from 40:60 to 25:75.

A preferred combination is DPT according to the invention in a mixture with one or more esters of cyclohexanedicarboxylic acid, especially with the 1,2-, 1,3- or 1,4-esters, of which the alkyl or alcohol radicals of the ester functions comprise 8 to 10 carbon atoms. Particular preference is given to using DPT according to the invention in a mixture with diisononyl cyclohexane-1,2-dicarboxylate or diisononyl cyclohexane-1,4-dicarboxylate.

Also favorable are combinations of DPT according to the invention with terephthalates comprising 8 to 10 carbon atoms in the alkyl or alcohol radicals of the ester function, especially with diisononyl terephthalate or diethylhexyl terephthalate. Also of advantage are combinations of DPT with furanoates of which the alkyl groups of the ester functions comprise 8 to 10 carbon atoms, combinations of DPT with alkylsulfonic acid esters of phenol or polyol esters such as pentaerythritol tetravalerate for example.

In one embodiment, DPT according to the invention is combined with $C_8$-$C_{10}$ phthalates, especially $C_9$- or $C_{10}$ phthalates. Particular preference here is given to combinations of DPT according to the invention with DINP (diisononyl phthalate), DIDP (diisodecyl phthalate) and/or DPHP (dipropylheptyl phthalate). These plasticizer mixtures preferably comprise less than 5% by mass and especially less than 0.5% by mass of other phthalate-containing compounds.

The present invention further relates to a plastisol comprising diisopentyl terephthalate according to the invention. This plastisol has the advantages described above, in particular a low plastisol viscosity and a good storage stability.

The plastisol preferably comprises one polymer or two or more polymers. Suitable polymers are preferably selected from the group consisting of polyvinyl chloride (PVC), homo- or copolymers based on ethylene, propylene, butadiene, vinyl acetate, glycidyl acrylate, glycidyl methacrylate, ethyl acrylate, butyl acrylate or methacrylate with alkoxy radicals of branched or unbranched alcohols having one to ten carbon atoms, acrylonitrile or cyclic olefins, polyvinylidene chloride (PVDC), polyacrylates, especially polymethyl methacrylate (PMMA), polyalkyl methacrylate (PAMA), polyureas, silylated polymers, fluoropolymers, especially polyvinylidene fluoride (PVDF), polytetrafluoroethylene (PTFE), polyvinyl acetate (PVAc), polyvinyl alcohol (PVA), polyvinyl acetals, especially polyvinyl butyral (PVB), polystyrene polymers, especially polystyrene (PS), expandable polystyrene (EPS), acrylonitrile-styrene acrylate (ASA), styrene-acrylonitrile (SAN), acrylonitrile-butadiene-styrene (ABS), styrene-maleic anhydride copolymer (SMA), styrene-methacrylic acid copolymer, polyolefins, especially polyethylene (PE) or polypropylene (PP), thermoplastic polyolefins (TPO), polyethylene-vinyl acetate (EVA), polycarbonates, polyethylene terephthalate (PET), polybutylene terephthalate (PBT), polyoxymethylene (POM), polyamide (PA), polyethylene glycol (PEG), polyurethane (PU), thermoplastic polyurethane (TPU), polysulphide (PSu), biopolymers, especially polylactic acid (PLA), polyhydroxybutyral (PHB), polyhydroxyvaleric acid (PHV), polyesters, starch, cellulose and cellulose derivatives, especially nitrocellulose (NC), ethylcellulose (EC), cellulose acetate (CA), cellulose acetate/butyrate (CAB), rubber and silicones.

Preferred polymers are polyvinyl chloride, copolymers of vinyl chloride with vinyl acetate or with butyl acrylate, polyalkyl methacrylate (PAMA), polyvinyl butyral (PVB), polyurethane, polysulphides, polylactic acid (PLA), polyhydroxybutyral (PHB) and nitrocellulose. Particular preference is given to PVC. Especially preferred are emulsion or microsuspension PVC.

In a preferred manner, the amount of DPT according to the invention in the plastisol is 5 to 120 parts by mass, preferably 10 to 100 parts by mass, particularly preferably 15 to 90 parts by mass and especially preferably 20 to 80 parts by mass per 100 parts by mass of polymer.

In one embodiment, the plastisol is processed to give a foam.

It is preferable in this case that the plastisol comprises a foam former. This foam former may be a compound that evolves gas bubbles which may optionally be used together with a so-called "kicker". Kickers of this kind generally refer to metal-containing compounds which catalyze the thermal decomposition of the component evolving gas bubbles and results in the foam former reacting with evolution of gas and foaming the plastisol. Foam formers are also referred to as blowing agents. In principle, the plastisol may be foamed chemically (i.e. by means of blowing agents) or mechanically (by incorporating gases, particularly air). The component evolving gas bubbles (blowing agent) that is used is preferably a compound which decomposes into gaseous constituents under the influence of heat and thus causes expansion of the plastisol.

Blowing agents for foaming suitable for the production of polymer foams include all known types of blowing agent, physical and/or chemical blowing agents including inorganic blowing agents and organic blowing agents.

Examples of chemical blowing agents are azodicarbonamide, azodiisobutyronitrile, benzenesulfonyl hydrazide, 4,4-oxybenzenesulfonyl semicarbazide, 4,4-oxybis(benzenesulfonyl hydrazide), diphenylsulfone-3,3-disulfonyl hydrazide, p-toluenesulfonyl semicarbazide, N,N-dimethyl-N,N-dinitrosoterephthalamide and trihydrazinetriazine, N,N'-dinitrosopentamethylenetetramine, dinitrosotrimethyltriamine, sodium hydrogencarbonate, sodium bicarbonate, mixtures of sodium bicarbonate and citric acid, ammonium carbonate, ammonium bicarbonate, potassium bicarbonate, diazoaminobenzene, diazoaminotoluene, hydrazodicarbonamide, diazoisobutyronitrile, barium azodicarboxylate and 5-hydroxytetrazole. The at least one blowing agent used is particularly preferably azodicarbonamide, which on reaction releases gaseous components such as $N_2$, $CO_2$ and CO. The decomposition temperature of the blowing agent may be reduced by the kicker.

Mechanically foamed compositions are also referred to as "beaten foam".

As an alternative to the processing of the plastisol to give a foam, this may also be further processed non-foamed (i.e. compact) to give a film or a coating for example. Preference is given to processing one or more different plastisols to give multi-layer systems in which one or more layers of foamed plastisol and one or more layers of non-foamed plastisol have been produced. Also feasible are multi-layer systems which have been produced exclusively from foamed plastisol or alternatively exclusively from non-foamed plastisol. It may be preferable in this case that only one of the layers comprises DPT according to the invention or that two or more layers of a corresponding multi-layer system comprises DPT according to the invention—optionally in a mixture with one or more other plasticizing compounds. Examples of multi-layer systems are artificial leather or CV floor coverings (CV=cushion vinyl). Furthermore, plastisols can be processed to produce gloves, toys such as dolls' heads (by rotation processes) for example, or also to underbody protection (by applying the plastisol to the vehicle underside).

Independently of the type of further processing, the plastisol may also comprise additives selected in particular from the group consisting of fillers/reinforcing agents, pigments, matting agents, heat stabilizers, costabilizers with plasticizing effect, antioxidants, UV stabilizers, costabilizers, solvents, viscosity regulators, foam stabilizers, flame retardants, adhesion promoters and processing auxiliaries (lubricants for example).

As already described, DPT according to the invention is particularly suitable for reducing the viscosity in plasticizer mixtures and plastisols. The DPT-containing mixtures including the resulting plastisols are also characterized by an improved storage stability. The present invention therefore further relates to the use of DPT according to the invention for lowering the viscosity and/or for improving the storage stability of plasticizer mixtures or plastisols.

The low viscosity of the DPT according to the invention even at low temperatures (for example at −40° C.) is particularly of advantage in those regions where temperatures prevail on the exterior of buildings, induced by climate, and also therefore in non-heated industrial plants, in which many materials are highly viscous or even solid. The present invention accordingly relates to the use of DPT according to the invention in the production of plastisols at ambient temperatures which are not reliably above 20° C. In preferred embodiments, the DPT according to the invention is used in the production of plastisols at ambient temperatures which are not reliably above 15° C., 10° C., 5° C., 0° C., −5° C. or even not reliably above −10° C. In the context of the present invention, a temperature is not reliably above a certain value if the temperature exceeds the specified value even only once per month or even only once within a year. Accordingly, a temperature is then reliably above a certain value if the temperature is always higher than the temperature specified.

The use of DPT according to the invention enables the saving of complex heating and insulating systems and also dispenses with the use of special pumps for highly viscous media since DPT according to the invention and also the plasticizer mixtures produced therefrom can be pumped without any difficulty even at low temperatures due to their low viscosity.

The DPT according to the invention, a plasticizer mixture comprising this DPT or a plastisol comprising the DPT according to the invention is preferably processed further to undersealing materials for vehicles, wall coverings, fabric coatings, artificial leather or floor coverings, particularly elastic floor coverings. The present invention relates to a product, in particular an underbody protection, a wall covering, a fabric coating, an artificial leather or a floor covering, which comprises DPT according to the invention. The product may alternatively also comprise a mixture of DPT according to the invention and at least one further plasticizer or a plastisol comprising DPT according to the invention.

Independently of whether it has been produced from a plastisol, the product may comprise a polymer or two or more polymers. Suitable polymers are preferably selected from the group consisting of polyvinyl chloride (PVC), homo- or copolymers based on ethylene, propylene, butadiene, vinyl acetate, glycidyl acrylate, glycidyl methacrylate, ethyl acrylate, butyl acrylate or methacrylate with alkoxy radicals of branched or unbranched alcohols having one to ten carbon atoms, acrylonitrile or cyclic olefins, polyvinylidene chloride (PVDC), polyacrylates, especially polymethyl methacrylate (PMMA), polyalkyl methacrylate (PAMA), polyureas, silylated polymers, fluoropolymers, especially polyvinylidene fluoride (PVDF), polytetrafluoroethylene (PTFE), polyvinyl acetate (PVAc), polyvinyl alcohol (PVA), polyvinyl acetals, especially polyvinyl butyral (PVB), polystyrene polymers, especially polystyrene (PS), expandable polystyrene (EPS), acrylonitrile-styrene acrylate (ASA), styrene-acrylonitrile (SAN), acrylonitrile-butadiene-styrene (ABS), styrene-maleic anhydride copolymer (SMA), styrene-methacrylic acid copolymer, polyolefins, especially polyethylene (PE) or polypropylene (PP), thermoplastic polyolefins (TPO), polyethylene-vinyl acetate (EVA), polycarbonates, polyethylene terephthalate (PET), polybutylene terephthalate (PBT), polyoxymethylene (POM), polyamide (PA), polyethylene glycol (PEG), polyurethane (PU), thermoplastic polyurethane (TPU), polysulphide (PSu), biopolymers, especially polylactic acid (PLA), polyhydroxybutyral (PHB), polyhydroxyvaleric acid (PHV), polyesters, starch, cellulose and cellulose derivatives, especially nitrocellulose (NC), ethylcellulose (EC), cellulose acetate (CA), cellulose acetate/butyrate (CAB), rubber and silicones.

Preferred polymers are polyvinyl chloride, copolymers of vinyl chloride with vinyl acetate or with butyl acrylate, polyalkyl methacrylate (PAMA), polyvinyl butyral (PVB), polyurethane, polysulphides, polylactic acid (PLA), polyhydroxybutyral (PHB) and nitrocellulose. Particular preference is given to PVC. Especially preferred are emulsion or microsuspension PVC.

The present invention further relates to the use of DPT according to the invention as plasticizer in plastic compositions, particularly in PVC-containing plastic compositions.

The DPT according to the invention is preferably used as plasticizer in adhesives, sealants, coating materials, paints, inks, plastisols, foams, artificial leather, floor coverings (e.g. top layer), roofing membranes, underbody protection, fabric coatings, cables, wire insulation, hoses, extruded articles, films, in the automotive interior sector, in wall coverings, liquid inks, toys, contact sheets, food packaging or medical articles, for example tubes or blood bags.

DPT according to the invention is preferably used as a fast fuser which enables plastisol to be produced and further processed at particularly low and therefore favorable processing temperatures.

Based on 100 parts by mass of polymer, preferred compositions comprise from 5 to 200, preferably from 10 to 150, parts by mass of plasticizer.

The present invention also relates to a method for preparing DPT according to the invention by esterifying terephthalic acid or transesterifying a terephthalic ester with a mixture of isomeric pentanols.

In the method according to the invention, preference is given to using less than 15% by weight, preferably less than 10% by weight, more preferably less than 5% by weight and especially less than 2% by weight or less than 1% by weight of alcohols comprising more or less than 5 carbon atoms, i.e. alcohols that are not pentanols. The figure in % by weight is based in this case on the sum total of all alcohols used in the method.

The pentanol mixture used in the method according to the invention preferably comprises less than 60 mol % n-pentanol. The minimum content of n-pentanol in the mixture of isomeric pentanols is preferably at least 2 mol %, preferably at least 10 mol %, more preferably more than 20 mol %, with more preference more than 22.5 mol % or even more than 25 mol %, more preferably more than 27.5 mol %, 30 mol % or even more than 35 mol %.

The preferred quantitative ratios and proportions of n-pentanol, 2-methylbutanol and 3-methylbutanol in the mixture of isomeric pentanols used in the method according to the invention corresponds to the quantitative ratios and proportions which have already been described beforehand for the alkyl radicals of the DPT according to the invention. To avoid repetitions, reference is made to the text passages above.

In the method according to the invention, particular preference is given to using a mixture of isomeric pentanols comprising more than 2 mol % and less than 60 mol % n-pentanol and also pentanols having branched alkyl chains, wherein—based on the amount of all pentanols having branched alkyl chains present in the pentanol mixture—at least 50 mol %, preferably at least 60 mol %, especially at least 70 mol % are 2-methylbutanol.

If the mixtures according to the invention are prepared by transesterification, preferably one or more terephthalate esters in which the alkyl radicals of the ester functions each comprise fewer than 4 carbon atoms is/are transesterified with a mixture of isomeric pentanols.

By way of preference, dimethyl terephthalate or diethyl terephthalate, especially dimethyl terephthalate, is transesterified to give the mixtures of isomeric dipentyl terephthalates according to the invention.

The esterification or transesterification is preferably conducted in the presence of a catalyst or a plurality of catalysts, for example using Brønsted or Lewis acids or bases as catalyst. Particularly suitable catalysts have been found to be sulfuric acid, methanesulfonic acid, p-toluenesulfonic acid and metal compounds. Examples of particularly preferred catalysts are tin powder, tin(II) oxide, tin(II) oxalate, titanium catalysts such as tetraisopropyl orthotitanate, tetrabutyl orthotitanate or tetrapentyl orthotitanate, and also zirconium esters such as tetrabutyl zirconate or tetrapentyl zirconate. Examples of particularly preferred basic catalysts are alkoxides such as sodium methoxide and potassium methoxide.

In order to shift the equilibrium that develops in the reaction in favor of the mixtures according to the invention, it may be advantageous to distil the water that forms in the esterification or the alcohol that forms in the transesterification out of the reaction mixture. Preference is given to distilling off an azeotrope of water and alcohol. Because of possible foam formation, it is possible here to work with a column.

In addition, it may be advantageous to use the mixture of isomeric pentanols in an overall excess. Preference is given to using the mixture of isomeric pentanols in an excess of 5 to 50 mol %, especially 9 to 30 mol %, of the molar amount needed to form the mixture of dipentyl terephthalates according to the invention. With preference, the excess alcohol remaining after the reaction has ended is reused for a further esterification or transesterification or another chemical reaction. For this purpose, the excess alcohol can be worked up to increase its purity. For example, it is possible to at least partly condense an alcohol-water azeotrope that has been distilled off, to separate the condensate into an aqueous phase and an organic phase and to remove unwanted by-products—for example olefins formed by elimination of water from the alcohol—from the organic phase, before the organic phase that has then been purified is recycled into the reaction system or finds use for another reaction or for another purpose.

It is additionally possible to treat the reaction mixture from the esterification or transesterification with superheated alcohol vapor. In this way, it is possible to save a portion of the energy input through other media and to achieve good mixing of the reaction medium.

Other possibilities of saving energy are to feed the mixture of isomeric pentanols into the reaction system at a temperature above ambient temperature, for example at 40° C. or 60° C. It is also possible to use dimethyl terephthalate at elevated temperature, preferably in the form of a melt, in the method according to the invention. As well as the advantage of the energy input, this procedure additionally enables better mixing of the reaction medium and a reaction that proceeds more quickly.

After the esterification or transesterification reaction has ended, the particular reaction mixture is worked up in a customary manner. For example, it is possible to treat the crude ester with an aqueous base at an elevated pressure at least as high as the vapor pressure of water at the prevailing temperature. This process regime makes it possible to obtain reaction mixtures of good filterability.

EXAMPLES

Examples 1-8

Preparation of the Ester Mixtures

An apparatus comprising reaction flask equipped with stirrer, thermometer, attached 20 cm Raschig ring column with distillation head and receiving flask and immersion tube with dropping funnel attached, was filled with 485 g of dimethyl terephthalate (2.5 mol, 99.9% purity) and $m_{av}$ of alcohol A and $m_{bv}$ of alcohol B. The apparatus was flushed for one hour with nitrogen (6 l/h) via the immersion tube. Subsequently, 0.43 g of tetra-n-butyl titanate (1.25·10$^{-3}$ mol, Sigma Aldrich, >97% purity) was added. The reaction was heated to boiling temperature with stirring. From this time point methanol was produced which was continuously removed from the reaction via the distillation head. The methanol was removed at a head temperature of 65 to 68° C. Above 68° C., no methanol was removed from the system. Subsequently, further $m_{an}$ of alcohol A and $m_{bn}$ of alcohol B were metered in via the dropping funnel and the immersion tube such that the reaction temperature did not fall below 200° C. In the course of the transesterification, 160 g of methanol (5 mol) were produced.

After completion of the alcohol addition, samples were taken hourly from the reaction and analyzed by gas chromatography. As soon as less than 0.5 area % monomethyl mixed ester was detected by gas chromatography, the heating was switched off and a vacuum slowly applied (final vacuum 1 mbar). On reaching the final vacuum, the mixture was slowly heated up to 160° C. After removal of the excess alcohol, the heating was switched off and the reaction cooled to 80° C. under vacuum and introducing nitrogen. At this temperature, the acid number of the crude product was then determined.

A 3-fold stoichiometric amount of 10% aqueous sodium hydroxide (based on the theoretical amount of acid) was added to the crude product and the mixture stirred under nitrogen at 80° C. for 15 minutes. The mixture was then heated to 160° C. under reduced pressure and traces of low boilers present were removed with continuous introduction of nitrogen. Samples were taken hourly and analyzed by means of gas chromatography. After attaining below 0.025 area % residual alcohol in the sample according to gas chromatography, the product was again cooled to 80° C. and filtered by vacuum into a suction flask via a Buchner funnel with filter paper and precompressed filter cake of filter aid (Perlite type D14). Gas chromatographic analysis was in turn carried out on the filtrate to determine the purity (P) and the composition of the product.

TABLE 1

Details of the syntheses and resulting ester mixtures (Examples 1-8)

| | Alcohol A = n-pentanol | | Alcohol B = 2-methylbutanol | | Purity |
|---|---|---|---|---|---|
| | $m_{av}$ [g] | $m_{an}$ [g] | $m_{bv}$ [g] | $m_{bn}$ [g] | P [%] |
| Example 1 | 380.2 | 0 | 126.7 | 0 | 99.7 |
| Example 2 | 283.8 | 0 | 223.0 | 0 | 99.9 |
| Example 3 | 253.4 | 0 | 253.4 | 0 | 99.8 |
| Example 4 | 177.4 | 0 | 329.5 | 0 | 99.6 |
| Example 5 | 101.4 | 0 | 405.5 | 0 | 99.7 |

| | Alcohol A = n-butanol | | Alcohol B = 2-methylpropanol | | |
|---|---|---|---|---|---|
| | $m_{av}$ [g] | $m_{an}$ [g] | $m_{bv}$ [g] | $m_{bn}$ [g] | |
| Example 6 | 278.0 | 41.7 | 92.7 | 13.9 | 99.7 |
| Example 7 | 185.3 | 27.8 | 185.3 | 27.8 | 99.8 |
| Example 8 | 92.7 | 13.9 | 278.0 | 41.7 | 99.1 |

2-methylpropanol: Oxea, >99.5% purity
n-butanol: Sigma Aldrich, >99% purity
2-methylbutanol: Sigma Aldrich, >99.9% purity
n-pentanol: Sigma Aldrich, >99.9% purity The composition of the pentyl ester and butyl ester mixture may be determined by $^1$H-NMR and $^{13}$C-NMR. The NMR spectroscopy studies can in principle be conducted with any commercial NMR instrument.

In the present case, the composition of the mixtures was determined by $^1$H-NMR spectroscopy on a solution of the esters in deuterochloroform (CDCl$_3$). For the recording of the spectra, 20 mg of substance were dissolved in 0.6 ml of CDCl$_3$ (containing 1% by mass of TMS) and transferred to an NMR tube having a diameter of 5 mm. For the present NMR spectroscopy studies, an instrument of the Bruker Avance 500 type was used. The spectra were recorded at a temperature of 300 K with a delay of d1=5 seconds, 32 scans, a pulse length of about 9.5 μs (90° excitation pulse) and a sweep width of 10 000 Hz with a 5 mm BBO (broad band observer) sample head. The resonance signals were recorded against the chemical shift of tetramethylsilane (TMS=0 ppm) as internal standard. Other commercial NMR instruments give comparable results with the same operating parameters.

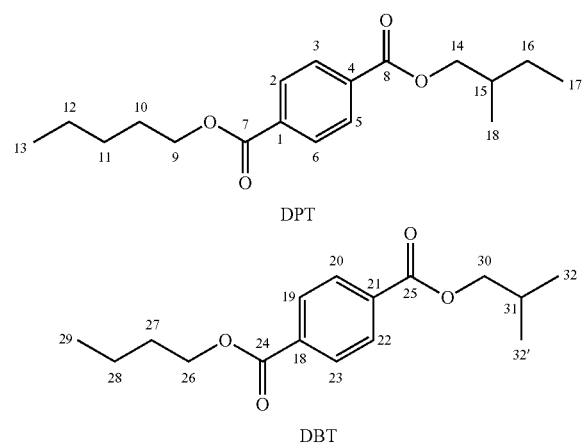

DPT

DBT

The resulting $^1$H-NMR spectra of the mixtures have resonance signals in the range from 4.0 to 4.5 ppm, which are due to the signals of the hydrogen atoms of the methylene groups directly adjacent to the oxygen of the alcohol or of the alcohol radical ($C^9H_2$ and $C^{14}H_2$; $C^{26}H_2$ and $C^{30}H_2$). Here, the protons of $C^9$ and $C^{26}$ experience a stronger downfield shift (triplet at ca. 4.35 ppm) than the protons of $C^{14}$ and $C^{30}$ (multiplet between 4.10 and 4.25 ppm). Quantification is effected by comparative determination of the area beneath the respective resonance signals, i.e. the area enclosed by the signal from the baseline. Commercial NMR instruments have devices for integration of the signal area. In the present NMR spectroscopy studies, the integration was conducted with the aid of the TopSpin® software, Version 3.1. The proportion of linear alkyl radicals in the respective ester mixture can be deduced by means of the following calculation.

$$\text{Mol \% } (n\text{-butyl radicals}) = \frac{I\ (C^{26}H_2)}{I\ (C^{26}H_2) + I\ (C^{30}H_2)} \times 100$$

$$\text{Mol \% } (n\text{-pentyl radicals}) = \frac{I\ (C^9H_2)}{I\ (C^9H_2) + I\ (C^{14}H_2)} \times 100$$

TABLE 2 ester mixtures investigated and the proportion of linear alkyl radicals in mol % according to NMR

| | Proportion of n-alcohol in the reaction mixture | Proportion of n-alkyl radical in the product | Designation |
|---|---|---|---|
| Example 1 | 75% | 77.4% | DPT (77% n) |
| Example 2 | 56% | 58.4% | DPT (58% n) |
| Example 3 | 50% | 52.9% | DPT (53% n) |
| Example 4 | 35% | 37.6% | DPT (38% n) |
| Example 5 | 20% | 20.6% | DPT (21% n) |
| Example 6 | 75% | 78.1% | DBT (78% n) |

TABLE 2-continued ester mixtures investigated and the proportion of linear alkyl radicals in mol % according to NMR

| | Proportion of n-alcohol in the reaction mixture | Proportion of n-alkyl radical in the product | Designation |
|---|---|---|---|
| Example 7 | 50% | 54.0% | DBT (54% n) |
| Example 8 | 25% | 27.8% | DBT (28% n) |

The ester mixtures from Table 2 were investigated in terms of application-relevant properties.

Example 9

Low Temperature Viscosity of the Ester Mixtures from Examples 1-8

The viscosities of the ester mixtures were determined on a Physica MCR 302 rheometer (Anton Paar Germany GmbH). In addition to the standard equipment, the rheometer has the following additional units:

Temperature-control device: CTD 450 Anton Paar Germany GmbH

Measurement system: PP 25 plate-plate system Anton Paar Germany GmbH

Nitrogen evaporator: EVU 10 Anton Paar Germany GmbH

Temperature control thermostat: Viscotherm VT2 Anton Paar Germany GmbH

Nitrogen reservoir: Apollo 100 Cryotherm GmbH & Co KG

The measurements were commenced at 25° C. The plate-plate measurement system, after setting the zero point, was adjusted to a measurement gap width of 0.5 mm. With the aid of a disposable pipette, the samples were applied to the plate system. In the trim position, it was tested whether the measurement gap had been filled with sufficient sample. The CTD 450 temperature-control device was closed and the jacket of the temperature-control device was adjusted to 23° C. with the aid of the thermostat.

A measurement program with the following parameters was created in the software.

Phase 1

Time setting 78 measurement points, phase duration 13 min

Measurement profile deformation amplitude gamma 0.1%; frequency f=10 Hz normal force $F_N$=0 N temperature $T_{[-1]}$=+25 . . . −40° C. linear Phase 2

Time setting 3 measurement points, phase duration 3 min

Measurement profile normal force $F_N$=0 N temperature $T_{[-1]}$=−40° C.

Phase 3

Time setting 78 measurement points, phase duration 13 min

Measurement profile deformation amplitude gamma 0.1%; frequency f=10 Hz normal force $F_N$=0 N temperature $T_{[-1]}$=−40 . . . +25° C. linear With the aid of the liquid nitrogen temperature control, the CTD 450 was now heated to 25° C. The measurement was initiated after a temperature stability of 1 minute at 25° C.±1° C.

The viscosities were evaluated by the rheology software Rheoplus 3.6.1. Firstly, the curve was freed of measurement errors by means of the automated "smoothing" and "merging" evaluation module in the evaluation program. By means of a further "interpolation" evaluation step, the temperature at 1000 Pa·s was determined as follows: logarithmic interpolation of the temperature (x-axis) in relation to the "viscosity value" (y-axis) of the smoothed curve. The temperatures determined in this manner at which the ester mixtures have a viscosity of 1000 Pa·s are compiled in Table 3.

The butyl ester mixture of terephthalic acid having 28% linear butyl radicals (DBT 28% n, Example 8) has a melting point above 25° C. Determination of the low temperature viscosity was therefore omitted.

The viscosity values obtained in measurement phase 3 were plotted against temperature (FIG. 1). The following information can be deduced from FIG. 1:
- the pentyl ester mixtures investigated having 38%, 53% and 58% linear pentyl radicals (DPT 38% n, DPT 53% n, DPT 58% n) show no notable changes to the viscosity in the temperature interval investigated (−40° C. (+override of the cooling) to 25° C.). The viscosities are consistently at values below 100 Pa·s. The ester mixtures can therefore be pumped without difficulty over the entire temperature range.
- the pentyl ester mixture having 21% linear pentyl radicals (DPT 21% n) solidifies (presumably due to kinetic factors) only on heating (to −32° C.) and then liquefies again at ca. 5° C. (viscosity below 1000 Pa·s).
- the pentyl ester mixture having 77% linear pentyl radicals (DPT 77% n) liquefies (viscosity less than 1000 Pa·s) at ca. 3° C.
- the butyl ester mixtures having 54% or 78% linear butyl radicals (DBT 54% n or DBT 78% n) liquefy (viscosity less than 1000 Pa·s) at ca. −5° C. or at ca. 0° C. respectively.
- explanation of the shoulders: variations due to density changes of the samples at variable measurement gap (normal force of the measurement system $F_N$=0).

TABLE 3

Temperature on reaching a viscosity of 1000 Pa · s from interpolation

| Ester mixture (proportion of linear alkyl radicals in %) | Temperature at 1000 Pa · s [° C.] |
|---|---|
| Dipentyl terephthalate (21% n) | 5.3 |
| Dipentyl terephthalate (38% n) | <−40.0 |
| Dipentyl terephthalate (53% n) | <−40.0 |
| Dipentyl terephthalate (58% n) | <−40.0 |
| Dipentyl terephthalate (77% n) | 3.2 |
| Dibutyl terephthalate (54% n) | −5.1 |
| Dibutyl terephthalate (78% n) | 0.1 |

Example 10

DSC of Various Dipentyl Terephthalate Mixtures

The DSC measurements (differential scanning calorimetry) are based on the proven Boersma or heat flow principle in which the heat flow to a sample and to a reference are compared. A highly sensitive ceramic sensor is used for measuring the difference between the heat flows. Using this principle, very small thermal changes in the sample can be determined. For example, glass transitions, melt transitions, crystallization transitions or boiling transitions decomposition transitions can be measured. It is not unusual that thermal transitions are close together. By modifications to some measurement parameters, these may be disaggregated.

The samples were measured in an aluminium crucible under nitrogen with a DSC 1 from Mettler Toledo using the following settings:

Drygas nitrogen: ca. 45 $l_s$/min

Gas nitrogen (purge gas): ca. 180 $l_s$/min

Cooling: liquid nitrogen (auxiliary reservoir 1.5 bar)

Method: Recrystallization

[1] 25.0 to 80.0° C., −1.0 K/min

[2] −80.0 to −120.0° C., −25.0 K/min

[3] −120.0° C., 3.00 min

[4] −120.0 to 100.0° C., 10.0 K/min

[5] 100 to 25.0° C., −30.0 K/min

The synchronized heating curves are shown in FIGS. 2 to 8. The heat flow in Watts per gram of sample is plotted as a function of temperature in degrees Celsius (Tendo). The evaluation of the curves is compared in Table 4 with the expected values.

TABLE 4

DSC evaluation of the dipentyl terephthalate mixtures

| Ester mixture (proportion of linear alkyl radicals) | Melting point (onset) | Enthalpy of fusion [J/g] measured ($H_{meas}$) | expected ($H_{exp}$) according to 1 | Boeck factor (BF) according to 2 |
|---|---|---|---|---|
| Dipentyl terephthalate (0% n) | 15.1° C. | 75.8 | 75.8 | 100 |
| Dipentyl terephthalate (21% n) | −13.6° C. | 86.1 | 93.4 | 92 |
| Dipentyl terephthalate (38% n) | −13.7° C. | 1.3 | 107.7 | 1 |
| Dipentyl terephthalate (53% n) | — | — | 120.3 | 0 |
| Dipentyl terephthalate (58% n) | −15.1° C. | 3.7 | 124.5 | 3 |
| Dipentyl terephthalate (77% n) | 3.6° C. | 99.1 | 140.5 | 71 |
| Dipentyl terephthalate (100% n) | 21.1° C. | 169.1 | 169.1 | 100 |

1: Calculation of the Expected Enthalpy of Fusion $H_{exp}$:

$$H_{exp} = H_{D^n PT} \cdot x n_{Pentyl} + H_{D(2\text{-}Methylbutyl)PT} \cdot x_{2\text{-}Methylbutyl}$$

where $H_{D\ n_{PT}}$: enthalpy of fusion of di-n-pentyl terephthalate $x\ n_{Pentyl}$: mole fraction of n-pentyl radicals of all pentyl radicals in the relevant DPT $H_{D(2\text{-}Methylbutyl)PT}$: enthalpy of fusion of di(2-methylbutyl) terephthalate $x_{2\text{-}Methylbutyl}$: mole fraction of 2-methylbutyl radicals of all pentyl radicals in the relevant DPT 2: Calculation of the Boeck Factor BF:

$$BF = \frac{H_{meas}}{H_{exp}} \cdot 100$$

where $H_{exp}$: calculated as described under 1

$H_{meas}$ measured enthalpy (at the temperature specified in the Table)

Example 11

Solidification and Turbidity Characteristics of the Ester Mixtures

The solidification characteristics of liquid substances are determined in accordance with ISO 1392 and largely corresponds to the freezing temperature method according to OECD (guideline 102, section 19) or the EU test method A.1 (section 1.4.3). The solidification behavior is determined by cooling the liquid sample with stirring and recording the temperature. When the sample or parts of the sample solidifies, the temperature briefly remains constant. This "temperature plateau" is documented. To determine the solidification behavior, 10 ml of liquid sample were charged in the sample vessel, the thermocouple was dipped into the liquid and the sample stirred with a magnetic stirrer. The thermostat was set to −50° C. and the sample cooled. A Julabo FN32 operated in the standard program is used for the cooling with ethanol as coolant. The temperature was recorded during the cooling. Two valid determinations were carried out and the mean value entered in Table 5.

The cloud point was determined in accordance with DIN EN 23015. This standard applies strictly only to petroleum products and defines a method for the determination of the cloud point of petroleum products. The cloud point is "the temperature at which a cloud of paraffin crystals (turbidity) first occurs in a liquid when this is cooled under the fixed test conditions" (DIN EN 23015:1994).

The cloud point specified in Table 5 corresponds to the temperature at which turbidity was observed for the first time in the sample vessel.

TABLE 5

Solidification characteristics and cloud point of the ester mixtures

| Ester mixtures (proportion of linear alkyl radicals) | Cloud point [° C.] | Temperature level solidification behavior [° C.] |
|---|---|---|
| Dipentyl terephthalate (21% n) | −5.4° C. | −9.6° C. |
| Dipentyl terephthalate (38% n) | no | −26.9° C. |
| Dipentyl terephthalate (53% n) | −27.9° C. | n.d. |
| Dipentyl terephthalate (58% n) | no | −28.2° C. |
| Dipentyl terephthalate (77% n) | −1.6° C. | −1.1° C. |

TABLE 5-continued

Solidification characteristics and cloud point of the ester mixtures

| Ester mixtures (proportion of linear alkyl radicals) | Cloud point [° C.] | Temperature level solidification behavior [° C.] |
|---|---|---|
| Dibutyl terephthalate (28% n) | 35.5° C. | 33.8° C. |
| Dibutyl terephthalate (54% n) | −5.6° C. | −9.7° C. |
| Dibutyl terephthalate (78% n) | −10.5° C. | −0.1° C. | n.d.: not determined
No: no cloud point was detected during the measurement

Example 12

Plastisol Production

PVC plastisols were produced, as used, for example, for the manufacture of topcoat films for floor coverings. The formulations of the plastisols are listed in Table 6.

TABLE 6

| Plastisol formulation | |
|---|---|
| PVC (Vestolit B 7021 - Ultra; from Vestolit) | 100 |
| Respective plasticizer from Table 2 | 50 |
| Epoxidized soybean oil as costabilizer (Drapex 39, from Galata) | 3 |
| Thermal stabilizer based on Ca/Zn (Reagens CLX/759/6PF, from Reagens) | 2 |

Figures in phr (phr=parts per hundred parts resin)

First the liquid constituents and then the pulverulent constituents were weighed out into a PE cup. Prior to addition to the PE cup, the dibutyl terephthalate (DBT 28% n) had been melted while the other plasticizers had been heated to 25° C. prior to addition. The mixture was stirred manually with an ointment spatula in such a way that no unwetted powder was present any longer. The mixing cup was then clamped into the clamping device of an evacuation vial of a dissolver stirrer (Kreiss). After dipping the stirrer into the mixture, the evacuation unit was closed and a negative pressure of below 20 mbar was produced with the aid of a vacuum pump. The mixture was stirred, the rotational speed being increased from ca. 400 to 2000 revolutions per minute. The mixture was stirred at high rotational speed until the temperature on the digital display of the thermal sensor reached 30° C. This ensured that the plastisol was homogenized with a defined energy input. The rotational speed was then reduced again to 400 revolutions per minute and the plastisol was vented for a further 9 minutes. After venting, the stirrer was then stopped and the evacuation vessel was again adjusted to ambient pressure. The finished plastisol was immediately equilibrated to 25° C. in a climate-controlled cabinet for further studies.

Example 13

Gelling Temperature of the Plastisols

The investigation of the gelling behavior of the plastisols was conducted with a Physica MCR 101 rheometer (Anton Paar Germany GmbH) in oscillation mode using a plate-plate measuring system (PP25). An additional heating hood was connected to the system in order to achieve a homogeneous heat distribution and uniform sample temperature.

The following parameters were set:

| Mode: | Temperature gradient | |
|---|---|---|
| | Start temperature | 25° C. |
| | End temperature | 180° C. |
| | Heating/cooling rate | 5° C./min |
| | Oscillation frequency | 4-0.1 Hz logarithmic ramp |
| | Cycle frequency omega: | 10 s$^{-1}$ |
| | Number of measurement points: | 63 |
| | Measurement point duration: | 0.5 min |
| | Automatic gap adjustment F: | 0N |
| | Constant measurement point duration | |
| | Gap width | 0.5 mm |

Analysis Procedure:

The spatula was used to apply a few grams of the plastisol to be analysed, free from air bubbles, to the lower plate of the analysis system. In doing so, it was ensured that, after the analysis system had been assembled, it was possible for some plastisol to exude uniformly out of the analysis system (not more than 6 mm in any direction). The heating hood was subsequently positioned over the sample and the analysis was started. The so-called complex viscosity of the plastisol was determined after 24 h (after storage of the plastisol at 25° C. in a temperature control cabinet from Memmert) as a function of temperature.

The measure considered for the gelling was a significant increase in the complex viscosity. The value used for comparison was therefore the temperature on attainment of a plastisol viscosity of 1000 Pa·s.

TABLE 7

Gelling of the plastisols after 24 h, temperature in ° C. on attainment of a plastisol viscosity of 1000 Pa · s (in short: gelling temperature)

| Ester mixture (proportion of linear alkyl radicals in %) | Gelling temperature [° C.] |
|---|---|
| Dipentyl terephthalate (21% n) | 71.7 |
| Dipentyl terephthalate (38% n) | 70.6 |
| Dipentyl terephthalate (53% n) | 70.2 |
| Dipentyl terephthalate (58% n) | 70.3 |
| Dipentyl terephthalate (77% n) | 70.0 |
| Dibutyl terephthalate (28% n) | 67.5 |
| Dibutyl terephthalate (54% n) | 65.7 |
| Dibutyl terephthalate (78% n) | 65.0 |

The plastisols of the pentyl esters have a slightly varying gelling temperature independent of the isomer distribution of the pentyl radicals, whereas the gelling temperature of the plastisols of the butyl esters scatters over a significantly wider range.

Example 14

Measurement of the Plastisol Viscosity

The viscosities of the plastisols produced in Example 12 were measured with a Physica MCR 301 rheometer (Anton Paar Germany GmbH) with the aid of the associated "Rheoplus Software" as follows.

The plastisol was stirred once again in the reservoir vessel with a spatula and measured in the measurement system Z3 (DIN 25 mm) according to operating instructions. The measurement proceeded automatically at 25° C. via the software mentioned above. The following points were controlled:

A pre-shear of 100 s$^{-1}$ for a period of 60 s, during which no measurements were taken.

A downward progression, starting at 200 s$^{-1}$ down to 0.1 s$^{-1}$, divided into a logarithmic series of 30 steps each with measurement point duration of 5 seconds.

The processing of the measurement data was carried out automatically by the software after the measurement. The viscosity as a function of the shear rate was displayed. The measurements were carried out in each case after 2 h, 24 h and 7 days. Between these time points, the paste was stored at 25° C.

The results of the measurement are shown in FIGS. 9 and 10. FIG. 9 illustrates the plastisol viscosity of the individual pastes after storage for 7 days at 25° C. as a function of the shear rate. FIG. 10 shows the change in the plastisol viscosity after storage in each case for 1 day and 7 days (at 25° C.), based on the viscosity of the plastisol heated only for 2 hours at 25° C. after their production, at shear rates of 1 s$^{-1}$, 10 s$^{-1}$ and 100 s$^{-1}$ in % (shown in %) and thereby allowing an evaluation of the thickening behavior of the plastisols.

The plastisols of the pentyl ester mixtures have lower viscosities after storage compared to the plastisols of the butyl ester mixtures. Moreover, the viscosities of the pentyl ester plastisols are characterized by high consistency—independently of the isomer distribution of the pentyl radicals—(FIG. 9). Within 7 days the pentyl ester plastisols thicken by less than 130% whereas the butyl ester plastisols without exception have a substantially greater thickening tendency (FIG. 10). Therefore, the pentyl ester plastisols are characterized by more consistent and therefore more reliable properties in comparison to the butyl ester plastisols both as a function of time and as a function of the isomer distribution of the alkyl radicals.

Examples 15-19

Preparation of Further Ester Mixtures

In analogy to the preparation of the esters from Examples 1-8, further ester mixtures were synthesized in which the alcohol mixture used comprised alcohol A in an amount $m_{av}$, alcohol B in an amount $m_{bv}$ and alcohol C in an amount $m_{cv}$. In these examples—as in Examples 1 to 5—the total amount of alcohol was used at the start and unlike in the preparation of Examples 6 to 8, no alcohol was metered in (corresponding to $m_{an}$ and $m_{bn}$ in the description of Examples 1 to 8 and in Table 1) after the start of the reaction ($m_{an}$, $m_{bn}$ and an analogous $m_{cn}$ are accordingly equal to zero in Examples 15 to 19 and are therefore not reported in Table 8). In experiments 15-19, 0.85 g of tetra-n-butyl titanate (Sigma Aldrich, purity>97%) was used. Additional modifications to the method described in Examples 1-8 were not carried out.

TABLE 8

Details of the syntheses and resulting ester mixtures (Examples 15-19)

| | Alcohol A = n-pentanol $m_{av}$ [g] | Alcohol B = 2-methylbutanol $m_{bv}$ [g] | Alcohol C = 3-methylbutanol $m_{bv}$ [g] | Purity R [%] |
|---|---|---|---|---|
| Example 15 | 253.9 | 0.0 | 253.9 | 99.5 |
| Example 16 | 253.9 | 139.3 | 113.7 | 99.7 |
| Example 17 | 253.4 | 190.4 | 63.4 | 99.6 |

TABLE 8-continued

Details of the syntheses and resulting
ester mixtures (Examples 15-19)

|  | Alcohol A = n-pentanol $m_{av}$ [g] | Alcohol B = 2-methylbutanol $m_{bv}$ [g] | Alcohol C = 3-methylbutanol $m_{bv}$ [g] | Purity R [%] |
|---|---|---|---|---|
| Example 18 | 253.9 | 215.1 | 37.9 | 99.6 |
| Example 19 | 218.0 | 216.9 | 72.0 | 99.6 |

2-methylbutanol: Sigma Aldrich, purity >99.9%
3-methylbutanol: Sigma Aldrich, purity >98.5%
n-pentanol: Sigma Aldrich, purity >99.9%

The calculation of the composition of the ester mixtures, as described in Examples 1 to 8, was carried out by NMR. Quantitative evaluation was conducted by $^1$H-NMR.

Quantification of the n-pentyl, 2-methylbutyl and 3-methylbutyl radicals in the ester mixture is achieved by determining the areas under the signals of the OCH$_2$ groups in the $^1$H-NMR. These signals occur at ca. 4.25 ppm (triplet) for the n-pentyl radicals, at ca. 4.04 to 4.17 (multiplet) for the 2-methylbutyl radicals and at ca. 4.29 ppm (triplet) for the 3-methylbutyl radicals. The proportion of the respective alkyl radicals in the ester mixture corresponds to the signal area of the alkyl radical under consideration in each case divided by the sum of the areas under the signals of all three alkyl radicals.

TABLE 9

Proportion of the different alkyl radicals in mol % according
to NMR in the ester mixtures of Examples 15-19

|  | Proportion of n-alkyl radicals in the product | Proportion of 2-methylbutyl radicals in the product | Proportion of 3-methylbutyl radicals in the product | Proportion of 2-methylbutyl radicals of branched alkyl radicals in the product |
|---|---|---|---|---|
| Example 15 | 51.0% | 0.0% | 49.0% | 0% |
| Example 16 | 47.6% | 28.3% | 24.1% | 54.0% |
| Example 17 | 50.8% | 38.4% | 10.8% | 78.0% |
| Example 18 | 49.6% | 42.6% | 7.8% | 84.5% |
| Example 19 | 43.3% | 44.3% | 12.4% | 78.1% |

Example 20

Low Temperature Viscosity of the Ester Mixtures of Examples 15-19

The viscosities of the ester mixtures of Examples 15-19 were determined as described in Example 9 using the same hardware and software. The only deviation from the method described in Example 9 was that a phase duration of 13 minutes was selected in measurement phase 2.

As in Example 9, the viscosity values obtained in measurement phase 3 were also plotted here against temperature (FIG. 11). The following information can be deduced from FIG. 11:

the pentyl ester mixtures investigated, in which the proportion of 2-methylbutyl radicals of the branched ester radicals are 78.1% (Example 19), 84.5% (Example 18) and 78.0% (Example 17), show no notable change in the viscosity in the temperature interval investigated (−40° C. (+override of the cooling) to 25° C.). The viscosities are consistently at values below 100 Pa·s. The ester mixtures can therefore be pumped without difficulty over the entire temperature range.

the pentyl ester mixture having a proportion of 54.0% 2-methylbutyl radicals of the branched ester radicals (Example 16) and the mixture comprising exclusively linear pentyl radicals and 3-methylbutyl radicals (Example 15) are solid at low temperatures and liquefy (viscosity less than 1000 Pa·s) at ca. −15.5° C. (Example 16) or at ca. 4° C. (Example 15).

explanation of the shoulders: variations due to density changes of the samples at variable measurement gap (normal force of the measurement system $F_N$=0).

TABLE 10

Temperature on reaching a viscosity
of 1000 Pa · s from interpolation

|  | Temperature at 1000 Pa · s [° C.] |
|---|---|
| Example 15 | −4.0 |
| Example 16 | −15.5 |
| Example 17 | <−40.0 |
| Example 18 | <−40.0 |
| Example 19 | <−40.0 |

The invention claimed is:

1. A mixture comprising diisopentyl terephthalate and a plasticizer, wherein the diisopentyl terephthalate comprises pentyl radicals of which, from more than 25 mol % to less than 60 mol % of the pentyl radicals are n-pentyl radicals, wherein the diisopentyl terephthalate comprises branched isomeric pentyl radicals wherein at least 60 mol % of the branched isomeric pentyl radicals are 2-methylbutyl radicals, and the plasticizer selected is from the group consisting of alkyl benzoates, dialkyl adipates, glycerol esters, trialkyl citrates, acylated trialkyl citrates, trialkyl trimellitates, glycol dibenzoates, esters of furandicarboxylic acid, dialkanoyl esters of dianhydrohexitols and dialkester of 1,2-, 1,3- or 1,4-cyclohexane dicarboxylic acid, wherein the mixture has a viscosity of less than 1000 Pa·s at temperatures above 10° C., and wherein the ratio of the diisopentyl terephthalate to the plasticizer is from 60:40 to 10:90.

2. The mixture according to claim 1, comprising 2-methylbutyl radicals based on the pentyl radicals and comprising pentyl radicals of which, from more than 35 mol % to less than 50 mol % of the pentyl radicals are n-pentyl radicals, and has a Boeck factor is less than 90, and the ratio of diisopentyl terephthalate to the plasticizer is from 50:50 to 20:80.

3. The mixture according to claim 1, wherein at least 95 mol % of the branched isomeric pentyl radicals incorporated in the ester mixture are 2-methylbutyl radicals and has a Boeck factor is less than 10 and wherein the ratio of diisopentyl terephthalate to the plasticizer is from 40:60 to 25:75.

4. The mixture according to claim 1, wherein the mixture has a viscosity of less than 500 Pa·s at temperatures above −5° C.

5. A plastisol comprising the mixture according to claim 1.

6. A product, in particular an underbody protection, a wall covering, an artificial leather, a fabric coating or a floor, comprising the mixture according to claim 1.

7. A polymer composition comprising the mixture according to claim 1 as plasticizers in polymer compositions, particularly in PVC-containing polymer compositions.

8. A viscosity modifier comprising the mixture according to claim 1 wherein the viscosity modifier lowers the viscosity and improves the storage stability of a plastisol.

9. A process for making a plastisol comprising the step of adding the mixture according to claim 1 to a polymer at ambient temperatures of 20° C.

10. The method for preparing the mixture according to claim 1 comprising the step of esterifying terephthalic acid or transesterifying a terephthalic ester with a mixture of isomeric pentanols.

11. A product selected from the group consisting of an underbody protection, a wall covering, an artificial leather, a fabric coating and a floor, comprising the mixture of claim 1.

12. A product selected from the group consisting of an underbody protection, a wall covering, an artificial leather, a fabric coating and a floor, comprising the plastisol of claim 5.

13. A polyvinyl chloride polymer comprising the mixture according to claim 1.

14. A plasticizer comprising the mixture according to claim 1.

15. A method for preparing the mixture according to claim 2 comprising the step of esterifying terephthalic acid or transesterifying a terephthalic ester with a mixture of isomeric pentanols.

16. A method for preparing the mixture according to claim 3 comprising the step of esterifying terephthalic acid or transesterifying a terephthalic ester with a mixture of isomeric pentanols.

17. A method for preparing the mixture according to claim 4 comprising the step of esterifying terephthalic acid or transesterifying a terephthalic ester with a mixture of isomeric pentanols.

18. The mixture according to claim 2, wherein at least 95 mol % of the branched isomeric pentyl radicals incorporated in the ester mixture are 2-methylbutyl radicals.

19. The mixture according to claim 3, wherein it has a viscosity of less than 1000 Pa·s at temperatures above −5° C.

* * * * *